United States Patent
Neri et al.

[11] Patent Number: 5,225,563
[45] Date of Patent: Jul. 6, 1993

[54] PHOTOCHROMATIC COMPOUND, A METHOD FOR ITS PREPARATION, AND ARTICLES WHICH CONTAIN IT

[75] Inventors: Carlo Neri; William Giroldini; Antonio Rinaldi, all of San Donato Milanese; Luciana Crisci, Sant'Angelo Lodigiano, all of Italy

[73] Assignee: Enichem Synthesis S.p.A., Palermo, Italy

[21] Appl. No.: 629,441

[22] Filed: Dec. 18, 1990

[30] Foreign Application Priority Data

Dec. 21, 1989 [IT] Italy .................. 22796 A/89

[51] Int. Cl.$^5$ .................. C07D 401/04; C07D 403/04; C07D 235/02
[52] U.S. Cl. .................. 546/271; 548/302.1
[58] Field of Search .................. 548/326, 302.1; 546/271

[56] References Cited

U.S. PATENT DOCUMENTS 3,915,985  10/1975  Hayes .................. 548/302.1
4,340,607  7/1982  Toja et al. .................. 548/302.1

FOREIGN PATENT DOCUMENTS 3609320  9/1987  Fed. Rep. of Germany .

OTHER PUBLICATIONS

Curt W. Beck et al., Chemical Abstracts, vol. 68, No. 5, No. 21882h (Jan. 29, 1968).

Chemishce Berichte, vol. 102, No. 12, Weinheim, DE and K. Volkamer et al. pp. 4177–4187 Jul. 1969.

*Primary Examiner*—Mary C. Lee
*Assistant Examiner*—Lenora Miltenberger
*Attorney, Agent, or Firm*—George P. Hoare, Jr.

[57] ABSTRACT

A photochromatic compound represented by the following general formula (I):

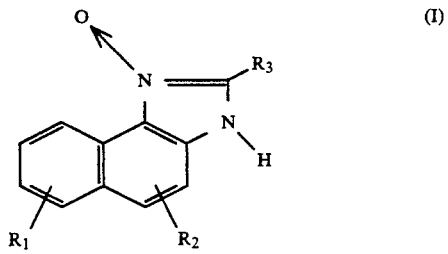

where:
$R_1$ and $R_2$ independently represent a linear, branched or cyclic C1–C10 alkyl radical, H, OH, F, Cl, Br, $NH_2$, $N(R_4)_2$, COOH, $OR_4$ or $COOR_4$ where $R_4$ is a C1–C10 linear, branched or cyclic alkyl radical, or an aryl radical;
$R_3$ is a variously substituted mono or polycondensed heterocyclic or aryl radical.

A compound (I) demonstrates marked photochromatic characteristics both when in an organic solvent solution and when incorporated into polymer matrices.

13 Claims, No Drawings

PHOTOCHROMATIC COMPOUND, A METHOD FOR ITS PREPARATION, AND ARTICLES WHICH CONTAIN IT

This invention relates to a photochromatic compound, the process for its preparation, and the photochromatic solutions and articles which contain it.

In particular, the invention relates to a derivative of naphthol (1,2) imidazole-1N-oxide, the process for its preparation and its use as a photochromatic compound.

Photochromatic compounds are substances having the characteristic of reversibly changing their colour and/or degree of light transmission when exposed to certain types of electromagnetic radiation and sunlight, to return to their original colour and light transmission state when the initial light source is removed. There are many known substances possessing photochromatic characteristics and pertain to various classes of inorganic and organic compounds, as described for example in "Photochromism", G.H. Brown (Ed.), vol. IV, of the Weissberger series "Techniques of Organic Chemistry", Wiley-Interscience, New York (1971). Certain imidazole 1-N-oxide derivatives have been described in the technical literature as photoinitiators for the oxidation of leuco dyes, such as the phenanthroimidazole-1-N-oxides described in patent application DE 3,609,320.

New compounds of the naphtho (1,2) imidazole-1N-oxide derivative class possessing photochromatic characteristics have now been found, which are obtainable by a simple and cost-effective process.

In accordance therewith, a first aspect of the present invention is the provision of a photochromatic compound definable by the following general formula (I):

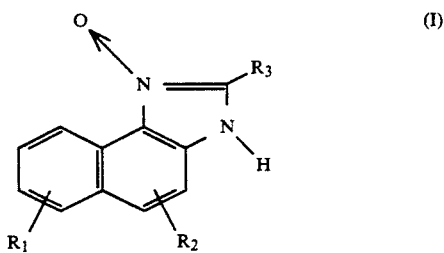

where:
$R_1$ and $R_2$ independently represent a linear, branched or cyclic C1-C10 alkyl radical, H, OH, F, Cl, Br, $NH_2$, $N(R_4)_2$, COOH, $OR_4$, $COOR_4$ where $R_4$ is a C1-C10 linear, branched or cyclic alkyl radical, or an aryl radical;
$R_3$ is a variously substituted mono or polycondensed heterocyclic or aryl radical.

According to the present invention the compound of general formula (I) can exist in its tautomer form (II):

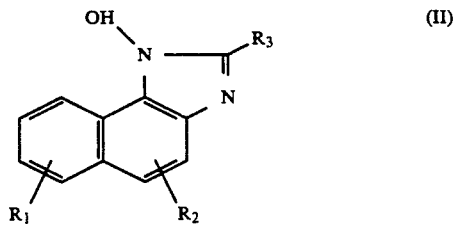

Thus by naphtho (1,2) imidazole-1N-oxide derivatives is meant both the compound defined by formula (I) or (II) and relative mixtures thereof.

In the preferred embodiment, the photochromatic compound according to the present invention is definable by the general formula (I) in which the substituents have the following meaning: $R_1$ and $R_2$ represent independently a hydrogen atom, COOH, $OCH_3$, OH or $NEt_2$; and $R_3$ represents:

an aryl radical of formula (III)

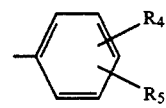

where $R_4$ and $R_5$ have the same meaning as $R_1$ and $R_2$;
a naphthyl radical of formula (IV)

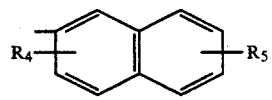

where $R_4$ and $R_5$ have the same meaning as $R_1$ and $R_2$;
an indole radical of formula (V)

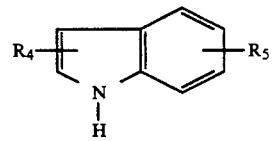

where $R_4$ and $R_5$ have the same meaning as $R_1$ and $R_2$; or
a pyridino radical of formula (VI)

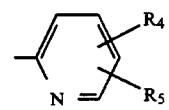

where $R_4$ and $R_5$ have the same meaning as $R_1$ and $R_2$.

Specific examples of preferred photochromatic compounds according to the present invention are:
F1: naphtho (1,2) imidazole-1N-oxide-2-(2-hydroxybenzene);
F2: naphtho (1,2) imidazole-1N-oxide-2-(4-hydroxybenzene);
F3: naphtho (1,2) imidazole-1N-oxide-2-(4-hydroxy-3,5-ditertbutylbenzene);
F4: naphtho (1,2) imidazole-1N-oxide-2-(2-hydroxy-4-N,N-diethylaminobenzene);
F5: naphtho (1,2) imidazole-1N-oxide-2-(4-N,N-diethylaminobenzene);
F6: naphtho (1,2) imidazole-1N-oxide-2-(3-indole);
F7: naphtho (1,2) imidazole-1N-oxide-2-(2-hydroxy-3-methoxybenzene);
F8: naphtho (1,2) imidazole-1N-oxide-2-(4-chlorobenzene);
F9: naphtho (1,2) imidazole-1N-oxide-2-(2-hydroxy-3,5-dichlorobenzene);
F10: naphtho (1,2) imidazole-1N-oxide-2-(2-hydroxy-3,5-ditertbutylbenzene);

F11: naphtho (1,2) imidazole-1N-oxide-2-(2-hydroxy-3,5-dimethylbenzene);
F12: naphtho (1,2) imidazole-1N-oxide-2-(1-hydroxy-4-chloro-2-naphthalene);
F13: 7-hydroxy-naphtho (1,2) imidazole-1N-oxide-2-(2-hydroxy-3,5-ditertbutylbenzene);
F14: 7-methoxy-naphtho (1,2) imidazole-1N-oxide-2-(3-indole);
F15: 7-methoxy-naphtho (1,2) imidazole-1N-oxide-2-(4-hydroxy-3,5-ditertbutylbenzene);
F16: 7-carboxy-naphtho (1,2) imidazole-1N-oxide-2-(3-indole);
F17: 5-(N-diethylamino)-naphtho (1,2) imidazole-1N-oxide-2-(4-hydroxybenzene);
F18: naphtho (1,2) imidazole-1N-oxide-2-(2,6-dichlorobenzene).

Of the aforesaid compounds those particularly preferred are the compounds numbered F1, F2, F3, F4, F5, F6, F7, F12, F14 and F15.

The following numbering has been used in describing the compounds of the present invention:

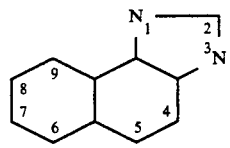

The photochromatic compound (I) according to the present invention is prepared by a process comprising:
a) reacting in an organic solvent in the presence of ammonia and an ammonium salt, and possibly a catalyst, the 1-nitroso-2 naphthol compound representable by the formula (VII):

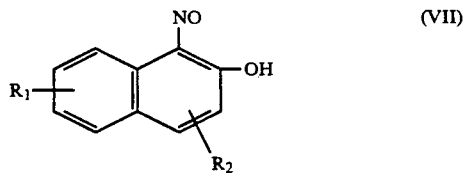

with an aldehyde $R_3$—CHO where $R_1$, $R_2$ and $R_3$ have the aforesaid meaning; and finally
b) isolating the desired product (I) from the reaction mixture obtained in stage a) and purifying it.

A compound of formula (VII) can be obtained by operating in accordance with one of the conventional methods of this particular sector, such as that described in Italian patent application No. 23007/A 84.

Examples of compounds of formula (VII) which are particularly suitable for the purposes of the present invention are:
1-nitroso-2-hydroxynaphthalene;
1-nitroso-2,6-dihydroxynaphthalene;
1-nitroso-2-hydroxy-6-methoxynaphthalene;
1-nitroso-2-hydroxy-6-carboxynaphthalene;
1-nitroso-2-hydroxy-4-N,N-diethylaminonaphthalene.

Examples of aldehydes suitable for the purposes of the present invention include:
2-hydroxybenzaldehyde;
4-hydroxybenzaldehyde;
2-hydroxy-3-methoxybenzaldehyde;
2-hydroxy-3,5-dichlorobenzaldehyde;
2-hydroxy-3,5-ditertbutylbenzaldehyde;
4-hydroxy-3,5-ditertbutylbenzaldehyde;
2-hydroxy-4-N,N-diethylaminobenzaldehyde
4-N,N-diethylaminobenzaldehyde
3-indolealdehyde;
2,6-dichlorobenzaldehyde;
1-hydroxy-4-chloro-2-naphthaldehyde;
2-pyridinealdehyde;
4-chlorobenzaldehyde.

In stage a) of the process according to the invention the condensation reaction is conducted by dissolving the compound (VI) and the aldehyde (the reagents) in a molar ratio equal or approximately equal to 1:1 in the organic solvent.

The reaction is conducted in the presence of ammonia and an ammonium salt in a molar ratio with respect to the two reagents of between 0.5:1 and 2:1 and between 0.3:1 and 0.9:1 respectively.

The procedure is carried out at a temperature of between 70° and 110° C. for a time of between 2 and 3 hours.

The operating temperature is preferably 100° C.

Examples of ammonium salts particularly suitable for the purposes of the present invention are ammonium chloride, ammonium acetate, ammonium sulphate, ammonium trifluoroacetate, ammonium p-toluenesulphonate and ammonium metasulphonate.

Suitable solvents are generally chosen from the alcohol, nitrile and ether groups.

Examples of said solvents are methanol, ethanol, isopropanol, n-butanol, acetonitrile, dioxane and tetrahydrofuran.

According to a preferred embodiment of the present invention the condensation reaction of stage a) can be conducted in the presence or absence of an acid catalyst depending on the reactivity of the aldehyde used.

In practice when using very reactive aldehydes such as 2-hydroxybenzaldehyde, 2,6-dichlorobenzaldehyde and 4-hydroxybenzaldehyde, the reaction is conducted in the absence of catalyst.

In the case of less reactive aldehydes the condensation reaction is conducted in the presence of a catalyst chosen from inorganic or organic acids such as sulphuric acid, hydrochloric acid, acetic acid, trifluoroacetic acid and methanesulphonic acid.

Acetic acid and trifluoroacetic acid are preferably used.

According to the process of the present invention said catalyst is used in a quantity such that its molar ratio to the compound of formula (VII) is between 1:10 and 1:2.

On termination of the condensation reaction the intermediate products are in no case isolated.

In stage b) of the process of the present invention the products of formula (I) are isolated from the reaction mixture by extraction in an alkaline phase, in which said products are soluble, and precipitation from the aqueous phase using a mineral or organic acid.

In certain cases (see Example 2) the pure product is isolated directly by filtration from the crude reaction product. The thus isolated products are finally purified by crystallization from suitable solvents generally chosen from ketones, alcohols or dimethylformamide.

The compounds of general formula (I) according to the present invention show marked photochromatic properties (Table I). Thus said compounds are useful for the preparation of photochromatic articles. In particular, said compounds can be incorporated into transparent or opaque organic polymers by methods depending on the polymer used.

According to the present invention the polymers can be chosen from polymethylmethacrylate, polyvinylalcohol, polyvinylpyrrolidone, cellulose butyrate acetate, epoxy resins, polysiloxane resins, polyurethane resins, polycarbonate and poly diethyleneglycol bis(allyl carbonate).

The compounds of formula (I) according to the present invention can be used in the production of photosensitive paper for protecting confidential documents against copying.

The following experimental examples are provided as non-limiting illustration of the invention.

EXAMPLE 1

Synthesis of naphtho (1,2) imidazole-1N-oxide-2-(2-hydroxybenzene)

87 g (0.5 moles) of 1-nitroso-2-naphthol, 61 g (0.5 moles) of 2-hydroxybenzaldehyde, 200 ml of methanol, 70 ml of a 33% aqueous NH$_4$OH solution and 20 g of ammonium chloride were introduced into an pressure vessel of 500 ml capacity. The resultant mixture was maintained at 100° C. for 3 hours and then cooled to ambient temperature (20°-25° C.).

The solvent was then evaporated from said mixture by distillation (about 150 ml recovered) to obtain a crude residue which was added to an aqueous solution (600 ml) of NaOH (40 g).

The resultant solution was heated to boiling in the presence of activated carbon and maintained at this temperature for 10 minutes. The solution was then filtered under cold conditions and was then slowly added to a mixture of acetic acid (60 g), water (200 g) and ethyl acetate (100 ml).

The precipitate obtained was separated by filtration and washed with water and ethyl acetate.

78 g of crude product were obtained and then purified by crystallization from dimethylformamide. The product structure was confirmed by mass spectrometry (MW=276) and infrared spectrometry.

EXAMPLE 2

Synthesis of naphtho (1,2) imidazole-1N-oxide-2-(4-hydroxy-3,5-ditertbutylbenzene)

70 g (0.4 moles) of 1-nitroso-2-naphthol, 90 g (0.385 moles) of 3,5-ditertbutyl-4-hydroxybenzaldehyde, 250 ml of ethanol and 65 ml of 33% NH$_4$OH were introduced into an pressure vessel of 500 ml capacity. After maintaining the mixture at 100° C. for 2 hours the solvent was removed by distillation. 250 ml of ethanol, 30 g of NH$_4$Cl and 10 g of CF$_3$COOH were then added to the crude residue and the resultant mixture was maintained at 100° C. for a further 2 hours.

On termination of this period, the residual solvent was removed and 250 ml of toluene were added to the mixture. After cooling, the precipitate obtained was separated by filtration and washed firstly with water and toluene and then with hexane. The crude product obtained (80 g) was purified by crystallization from methylethylketone.

The product structure was confirmed by mass spectrometry (MW=388) and infrared spectrometry.

EXAMPLE 3

Synthesis of naphtho (1,2) imidazole-1N-oxide-2-(3-indole)

70 g (0.4 moles) of 1-nitroso-2-naphthol, 58 g (0.4 moles) of 3-indolealdehyde, 250 ml of ethanol and 70 ml of 33% NH$_4$OH were introduced into an pressure vessel of 500 ml capacity. After maintaining the mixture at 100° C. for 2 hours the solvent (200 ml) was removed by distillation, and 250 ml of ethanol, 20 g of NH$_4$Cl and 15 g of CF$_3$COOH were then added to the crude residue.

The resultant mixture was maintained at 100° C. for 1.5 hours and then cooled to ambient temperature (20°-25° C.). 200 ml of butanol were added to the cooled mixture to obtain a precipitate which was separated by filtration. Said precipitate was then dissolved under cold conditions in an aqueous solution (500 ml) of NaOH (15 g) containing activated carbon. The mixture thus obtained was heated to boiling for 5 minutes, cooled and then filtered under cold conditions. 100 ml of ethyl acetate and 22 g of CH$_3$COOH were then added to the resultant solution.

The crude precipitate was again filtered to obtain a crude product (95 g) which was purified by crystallization from methylethylketone.

The product structure was confirmed by mass spectrometry (MW=299) and infrared spectrometry.

EXAMPLE 4

Synthesis of naphtho (1,2) imidazole-1N-oxide-2-(2-hydroxy-4-N,N-diethylaminobenzene)

87 g (0.5 moles) of 1-nitroso-2-naphthol, 96 g (0.5 moles) of 2-hydroxy-4-N,N-dimethyl-amino benzaldehyde, 250 ml of ethanol and 85 ml of 33% NH$_4$OH were introduced into an pressure vessel of 500 ml capacity.

After maintaining the mixture at 100° C. for 2 hours the solvent (200 ml) was removed by distillation, and 250 ml of ethanol, 28 g of NH$_4$Cl and 20 g of CF$_3$COOH were then added to the residue.

The mixture was heated to 100° C. and maintained at this temperature for a further 2 hours. The residual solvent was then removed by distillation and the crude reaction product was dissolved cold in an aqueous solution (800 ml) of NaOH (50 g) containing activated carbon. After keeping the mixture boiling for 5 minutes the solution was cooled and then filtered.

100 ml of ethyl acetate and 45 g of acetic acid were added to the resultant solution to obtain a precipitate which was separated by filtration.

The crude product obtained (105 g) was purified by crystallization from methylethylketone.

The product structure was confirmed by mass spectrometry (MW=347) and infrared spectrometry.

EXAMPLE 5

Synthesis of naphtho (1,2) imidazole-1N-oxide-2-(2-hydroxy-3-methoxybenzene);

87 g (0.5 moles) of 1-nitroso-2-naphthol, 76 g (0.5 moles) of 2-hydroxy-3-methoxy-benzaldehyde, 250 ml of ethanol and 85 ml of 33% NH$_4$OH were introduced into an pressure vessel of 500 ml capacity.

The procedure of Example 4 was followed to finally obtain 95 g of crude product which was purified by crystallization from methylethylketone.

The product structure was confirmed by mass spectrometry (MW=306) and infrared spectrometry.

EXAMPLE 6

Synthesis of naphtho (1,2) imidazole-1N-2-oxide-(4-N,N-diethylaminobenzene)

87 g (0.5 moles) of 1-nitroso-2-naphthol, 88 g (0.5 moles) of 4-N,N-diethylaminobenzene, 250 ml of ethanol and 85 ml of 33% $NH_4OH$ were introduced into an pressure vessel of 500 ml capacity.

The procedure of Example 4 was followed to finally obtain 80 g of crude product which was purified by crystallization from dimethylformamide.

The product structure was confirmed by mass spectrometry (MW=331) and infrared spectrometry.

EXAMPLE 7

Synthesis of naphtho (1,2) imidazole-1N-oxide-2-(4-hydroxybenzene)

87 g (0.5 moles) of 1-nitroso-2-naphthol, 61 g (0.5 moles) of 4-hydroxybenzaldehyde, 200 ml of methyl alcohol, 70 ml of 33% $NH_4OH$ and 20 g of $NH_4Cl$ were introduced into an pressure vessel of 500 ml capacity.

The procedure of Example 1 was followed to finally obtain 70 g of crude product which was purified by crystallization from dimethylformamide/isopropanol.

The product structure was confirmed by mass spectrometry (MW=276) and infrared spectrometry.

EXAMPLE 8

Synthesis of naphtho (1,2) imidazole-1N-oxide-2-(4-chlorobenzene)

87 g (0.5 moles) of 1-nitroso-2-naphthol, 70 g (0.5 moles) of 4-chlorobenzaldehyde, 180 ml of ethanol, 70 ml of 33% $NH_4OH$ and 18 g of $CH_3COONH_4$ were introduced into an pressure vessel of 500 ml capacity. The mixture was maintained at 100° C. for 3.5 hours and the solvent was separated by partial distillation. The crude residue thus obtained was added to 500 ml of water containing 30 g of NaOH and activated carbon.

The mixture was kept boiling for 5 minutes, filtered and the filtrate extracted with toluene (100 ml).

The aqueous phase was then added dropwise to a stirred mixture of acetic acid (45 g), water (150 ml) and ethyl acetate (100 ml), the precipitate obtained being then separated by filtration and washed with water and ethyl acetate.

The crude product obtained (60 g) was purified by crystallization from acetone.

The product structure was confirmed by mass spectrometry (MW=294) and infrared spectrometry.

EXAMPLE 9

Physico-chemical tests on the synthesized products

The naphtho (1,2) imidazole-1N-oxide derivatives generally show photochromatic behaviour, i.e. their UV-visible absorption spectrum in solution changes substantially after brief exposure (of the order of 10-30 seconds) to sunlight or to an artificial light source equivalent to sunlight.

In their deactivated form these compounds are generally colourless or barely yellow, whereas in their activated form the colour varies from red to brown to intense yellow or olive green. This effect is reversible and in the dark they return to their deactivated form, with kinetics varying according to the substituents in position 2 of the naphthoimidazole-1N-oxide and the substituents on the naphthalene rings. The return kinetics and colour in their activated form also depend on the polarity of the solvent and the presence of acid or basic groups in the solution or polymer to which the photochromatic compound has been added.

The photochromism of some of the synthesized compounds is shown in Table I

TABLE I

| Compound | Molecular weight | ΔY | λmax |
|---|---|---|---|
| F1 | 276 | 17.8 | 500 nm |
| F2 | 276 | 2.7 | 400 nm |
| F3 | 388 | 2.3 | 380 nm |
| F4 | 347 | 16.5 | 450 nm |
| F5 | 331 | 10.4 | 440 nm |
| F6 | 299 | 5.4 | 400 nm |
| F7 | 306 | 13.2 | 440 nm |
| F8 | 294 | 1.4 | 400 nm |

The measurements were made by dissolving the compounds in ethyl alcohol to a concentration of 0.001M and irradiating the resultant solution for 4 minutes with a high pressure mercury UV lamp and a No. 31 UV filter.

The symbol ΔY represents the variation in the light tansmittance of the system between the deactivated form and the activated form within the wavelength range of 360-770 nm.

ΔY is normally considered an index proportional to the photochromatic activity of a product.

The symbol λmax represents the maximum visible absorption of the activated form.

EXAMPLE 10

Photochromism in polymer material

The compounds F1 and F5 were incorporated into polymethylmethacrylate to a concentration of 0.1%. Activation was then effected for 4 minutes with a high pressure UV lamp and No. 31 UV filter, to obtain a ΔY of 6.0 (F1) and 1.0 (F5) for the materials containing said compounds.

EXAMPLE 11

Photochromism on paper The compounds F2, F3, F4 and F6 were applied to paper as a 0.03M methylethylketone solution, without the addition of additives.

After evaporating the solvent the colour of the paper varied from white to barely yellow. The paper was then activated by exposure to sunlight (intensity 10,000 lux) for 20 seconds, or by the lamps used in photocopiers. The colour for the various compounds varied as shown in Table II:

TABLE II

| Compound | Molecular weight | Colour obtained |
|---|---|---|
| F2 | 276 | dark brown |
| F3 | 388 | dark brown |
| F4 | 347 | light brown |
| F6 | 299 | green-brown |

We claim:

1. A photochromatic compound represented by the following formula (I):

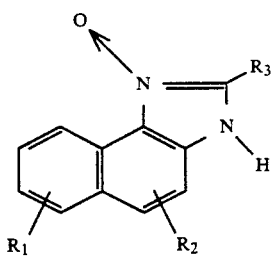

(I)

where:

R₁ and R₂ independently represent a linear, branched or cyclic C1-C10 alkyl radical, H, OH, F, Cl, Br, NH₂, N(R₄)₂, COOH, OR₄ or COOR₄ where R₄ is a C1-C10 linear, branched or cyclic alkyl radical, or an aryl radical;

R₃ is a phenyl, naphthyl, indole or pyridine.

2. A compound as claimed in claim 1, represented by the tautomer form (II):

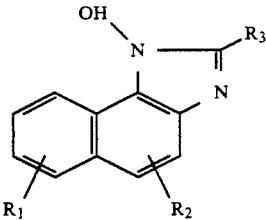

(II)

where:

R₁ and R₂ independently represent a linear, branched or cyclic C1-C10 alkyl radical, H, OH, F, Cl, Br, NH₂, N(R₄)₂, COOH, OR₄ or COOR₄ where R₄ is a C1-C10 linear, branched or cyclic alkyl radical, or an aryl radical; R₃ is a phenyl, naphthyl, indole or pyridine.

3. A compound as claimed in claim 1, wherein R₁ and R₂ represent independently a hydrogen atom, COOH, OCH₃, OH or NEt₂; and R₃ represents:

an aryl radical of formula (III)

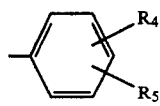

where R₄ and R₅ have the same meaning as R₁ and R₂;

a naphthyl radical of formula (IV)

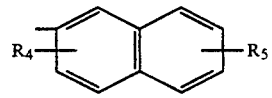

where R₄ and R₅ have the same meaning as R₁ and R₂;

an indole radical of formula (V)

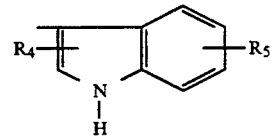

where R₄ and R₅ have the same meaning as R₁ and R₂; or a pyridino radical of formula (VI)

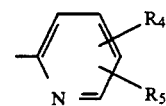

where R₄ and R₅ have the same meaning as R₁ and R₂.

4. A compound as claimed in claim 1, having the name F1: naphtho (1,2) imidazole-1N-oxide-2-(2-hydroxybenzene).

5. A compound as claimed in claim 1, having the name F2: naphtho (1,2) imidazole-1N-oxide-2-(4-hydroxybenzene).

6. A compound as claimed in claim 1, having the name F3: naphtho (1,2) imidazole-1N-oxide-2-(4-hydroxy-3,5-ditertbutylbenzene).

7. A compound as claimed in claim 1, having the name F4: naphtho (1,2) imidazole-1N-oxide-2-(2-hydroxy-4-N,N-diethylaminobenzene).

8. A compound as claimed in claim 1, having the name F5: naphtho (1,2) imidazole-1N-oxide-2-(4-N,N-diethylaminobenzene).

9. A compound as claimed in claim 1, having the name F6: naphtho (1,2) imidazole-1N-oxide-2-(3-indole).

10. A compound as claimed in claim 1, having the name F7: naphtho (1,2) imidazole-1N-oxide-2-(2-hydroxy-3-methoxybenzene).

11. A compound as claimed in claim 1, having the name F12: naphtho (1,2) imidazole-1N-oxide-2-(1-hydroxy-4-chloro-2-naphthalene).

12. A compound as claimed in claim 1, having the name F14: 7-methoxy-naphtho (1,2) imidazole-1N-oxide-2-(3-indole).

13. A compound as claimed in claim 1, having the name F15: 7-methoxy-naphtho (1,2) imidazole-1N-oxide-2-(4-hydroxy-3,5-ditertbutylbenzene).

* * * * *